United States Patent
Nozawa et al.

(10) Patent No.: US 10,881,288 B2
(45) Date of Patent: Jan. 5, 2021

(54) OPHTHALMIC APPARATUS

(71) Applicant: Tomey Corporation, Nagoya (JP)

(72) Inventors: Yuji Nozawa, Nagoya (JP); Takashi Sugaya, Nagoya (JP); Chihiro Kato, Nagoya (JP)

(73) Assignee: TOMEY CORPORATION, Nagoya (JP)

( * ) Notice: Subject to any disclaimer, the term of this patent is extended or adjusted under 35 U.S.C. 154(b) by 0 days.

(21) Appl. No.: 16/722,606

(22) Filed: Dec. 20, 2019

(65) Prior Publication Data

US 2020/0205654 A1 Jul. 2, 2020

(30) Foreign Application Priority Data

Dec. 28, 2018 (JP) .................. 2018-247624

(51) Int. Cl.
*G01B 9/02* (2006.01)
*A61B 3/00* (2006.01)

(52) U.S. Cl.
CPC ........ *A61B 3/0025* (2013.01); *G01B 9/02004* (2013.01); *G01B 9/0209* (2013.01); *G01B 9/02017* (2013.01); *G01B 9/02024* (2013.01); *G01B 9/02041* (2013.01); *G01B 9/02083* (2013.01)

(58) Field of Classification Search
CPC ..... A61B 3/0025; A61B 3/102; A61B 5/0066; G01B 9/02004; G01B 9/02041; G01B 9/02044; G01B 9/02083; G01B 9/02091; G01B 9/02069
See application file for complete search history.

(56) References Cited

U.S. PATENT DOCUMENTS

2014/0029012 A1* 1/2014 Ogawa .................. G01M 11/31
356/477
2014/0376000 A1* 12/2014 Swanson ............ G01B 9/02091
356/479

(Continued)

FOREIGN PATENT DOCUMENTS

EP 2949264 A1 12/2015
JP 2012-200283 A 10/2012

(Continued)

*Primary Examiner* — Tarifur R Chowdhury
*Assistant Examiner* — Jonathon Cook
(74) *Attorney, Agent, or Firm* — Shumaker, Loop & Kendrick, LLP

(57) ABSTRACT

An ophthalmic apparatus that includes a light source of wavelength sweeping type; a measurement optical system; a reference optical system; a light receiving element that receives interference light; a sample clock signal generator that generates a sample clock signal from the light from the light source, the sample clock signal cyclically changing at equal frequency intervals; a signal processor that samples an interference signal based on the sample clock signal, the interference signal being outputted from the light receiving element when the light receiving element receives the interference light. The ophthalmic apparatus generates period data based on the sample clock signal, the period data indicating a relationship between a period of the sample clock signal and time; and determines a processing duration of the interference signal sampled at the signal processor based on the period data.

6 Claims, 8 Drawing Sheets

(56) References Cited

U.S. PATENT DOCUMENTS

| | | | |
|---|---|---|---|
| 2015/0241202 A1* | 8/2015 | Jiang | G01B 9/02083 356/479 |
| 2016/0025478 A1* | 1/2016 | Johnson | G01B 9/02069 702/191 |
| 2018/0140183 A1* | 5/2018 | Fukasawa | G01B 9/02091 |

FOREIGN PATENT DOCUMENTS

| | | |
|---|---|---|
| JP | 2012-239514 A | 12/2012 |
| JP | 2015-226608 A | 12/2015 |

* cited by examiner

US 10,881,288 B2

OPHTHALMIC APPARATUS

CROSS-REFERENCE

This application claims priority to Japanese Patent Application No. 2018-247624, filed on Dec. 28, 2018, the entire contents of which are incorporated herein by reference.

TECHNICAL FIELD

The technique disclosed herein relates to an ophthalmic apparatus. To be more precise, it relates to an ophthalmic apparatus configured to measure a subject eye by using optical interferometry.

BACKGROUND

Ophthalmic apparatuses configured to capture intraocular tomographic images of a subject eye by using optical interferometry have been developed. This type of ophthalmic apparatuses includes those using Fourier domain scheme using a wavelength sweeping type light source (so-called SS-OCT scheme). In the SS-OCT scheme, a wavelength of light outputted from the light source cyclically changes, and it is preferable to execute sampling in a same wavelength range each time the wavelength of the light from the light source undergoes one cycle of change. For example, an apparatus described in Japanese Patent Application Publication No. 2012-200283 detects light having a particular wavelength among light from a wavelength sweeping type light source by using a fiber Bragg grating (FBG). A detection signal is generated from the detected light having the particular wavelength, and a trigger signal that defines a timing to start sampling is generated based on this detection signal. By starting sampling of an interference signal based on the trigger signal generated as above, the interference signal is sampled in the same wavelength range each time the wavelength of the light undergoes one cycle of change.

SUMMARY

In the technique described in Japanese Patent Application Publication No. 2012-200283, the particular wavelength needs to be detected within the light from the light source to generate the trigger signal, thus expensive members such as the FBG had to be installed in the apparatus. The description herein discloses a technology for setting a processing duration of an interference signal sampled in a SS-OCT scheme without using expensive members.

An ophthalmic apparatus disclosed herein may comprise: a light source of wavelength sweeping type; a measurement optical system configured to irradiate a subject eye with light from the light source and to guide reflected light from the subject eye; a reference optical system configured to guide the light from the light source so as to use the light from the light source as reference light; a light receiving element configured to receive interference light, the interference light being a combination of the reflected light from the subject eye and the reference light; a sample clock signal generator configured to generate a sample clock signal from the light from the light source, the sample clock signal cyclically changing at equal frequency intervals; a signal processor configured to sample an interference signal based on the sample clock signal outputted from the sample clock signal generator, the interference signal being outputted from the light receiving element when the light receiving element receives the interference light; a processor; and a memory storing computer-readable instructions therein. The computer-readable instructions, when executed by the processor, may cause the ophthalmic apparatus to: generate period data based on the sample clock signal, the period data indicating a relationship between a period of the sample clock signal and time; and determine a processing duration of the interference signal sampled at the signal processor based on the period data.

BRIEF DESCRIPTION OF DRAWINGS

FIG. 6A shows a relationship between a time and the wavelength of the light outputted from the light source, FIG. 6B shows a relationship between the time and a signal intensity of the K-clock signal, FIG. 6C shows a relationship between the time and a period of the K-clock signal, and FIG. 6D shows a relationship between the time and a frequency of the K-clock signal.

FIG. 7A shows a relationship between the time and the wavelength of the light outputted from the light source, FIG. 7B shows a relationship between the time and the signal intensity of the K-clock signal, and FIG. 7C shows a relationship between the time and the period of the K-clock signal.

FIG. 8A shows a relationship between the time and the wavelength of the light outputted from the light source, FIG. 8B shows a relationship between the time and the signal intensity of the K-clock signal, and FIG. 8C shows a relationship between the time and the period of the K-clock signal.

DETAILED DESCRIPTION

Figure 1:
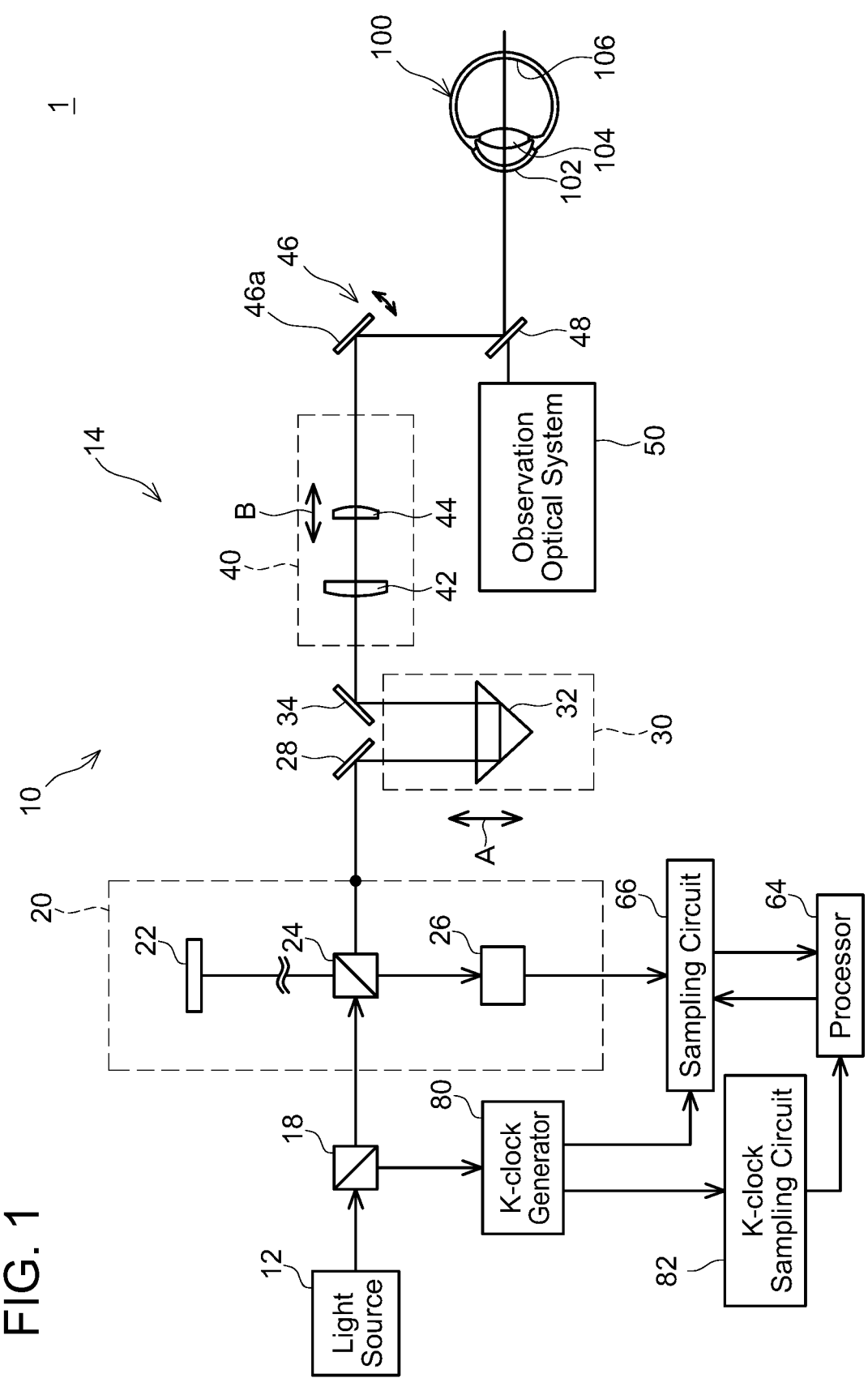
FIG. 1 shows a schematic configuration of an optical system of an ophthalmic apparatus according to an embodiment.

Representative, non-limiting examples of the present invention will now be described in further detail with reference to the attached drawings. This detailed description is merely intended to teach a person of skill in the art further details for practicing preferred aspects of the present teachings and is not intended to limit the scope of the invention. Furthermore, each of the additional features and teachings disclosed below may be utilized separately or in conjunction with other features and teachings to provide improved ophthalmic apparatuses, as well as methods for using and manufacturing the same.

Moreover, combinations of features and steps disclosed in the following detailed description may not be necessary to practice the invention in the broadest sense, and are instead taught merely to particularly describe representative examples of the invention. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Some of the features characteristic to below-described embodiments will herein be listed. It should be noted that the respective technical elements are independent of one another, and are useful solely or in combinations. The combinations thereof are not limited to those described in the claims as originally filed.

An ophthalmic apparatus disclosed herein may comprise: a light source of wavelength sweeping type; a measurement optical system configured to irradiate a subject eye with light from the light source and to guide reflected light from the subject eye; a reference optical system configured to guide the light from the light source so as to use the light from the light source as reference light; a light receiving element configured to receive interference light, the interference light being a combination of the reflected light from the subject eye and the reference light; a sample clock signal generator configured to generate a sample clock signal from the light from the light source, the sample clock signal cyclically changing at equal frequency intervals; a signal processor configured to sample an interference signal based on the sample clock signal outputted from the sample clock signal generator, the interference signal being outputted from the light receiving element when the light receiving element receives the interference light; a processor; and a memory storing computer-readable instructions therein. The computer-readable instructions, when executed by the processor, may cause the ophthalmic apparatus to: generate period data based on the sample clock signal, the period data indicating a relationship between a period of the sample clock signal and time; and determine a processing duration of the interference signal sampled at the signal processor based on the period data.

In the aforementioned ophthalmic apparatus, the sample clock signal generator is configured to generate the sample clock signal that cyclically changes at the equal frequency intervals. The ophthalmic apparatus is configured to be caused by the processor to generate the period data indicating the relationship between the time and the period of the sample clock signal based on the generated sample clock signal. Since the period-time relationship of the sample clock signal is identified, a frequency-time relationship of the sample clock signal can thereby be specified, and also a relationship between the time and the wavelength of the light from the light source can thereby be specified. Due to this, the processing duration of the interference signal sampled at the signal processor (for example, a duration of executing sampling in the signal processor) can be set based on the period data, and accordingly the interference signal sampled in a same wavelength range can be acquired each time the wavelength of the light from the light source undergoes one cycle of change. Thus, without installing separate members for detecting light of a particular wavelength, the processing duration of the interference signal sampled using the sample clock signal for sampling the interference signal can suitably be set.

In the ophthalmic apparatus disclosed herein, the light source may be configured to sweep a wavelength of light in a wavelength range ranging from a first wavelength to a second wavelength. The computer-readable instructions, when executed by the processor, further may cause the ophthalmic apparatus to detect one reference time at which the period is at its maximum or its minimum in the period data or two reference times including a time at which the period is at its maximum and a time at which the period is at its minimum in the period data, and the processing duration may be determined based on the detected reference time or the detected two reference times. According to this configuration, the wavelength sweeping type light source cyclically sweeps the wavelength of the light in the wavelength range ranging from the first wavelength to the second wavelength. Due to this, the period data of the sample clock signal generated from the light outputted from the wavelength sweeping type light source changes cyclically. Thus, the time at which the period is at its maximum or minimum appears cyclically, and by setting the processing duration of the interference signal sampled with this time as a reference, the interference signal sampled at the same timing each time the wavelength of the light undergoes one cycle of change can be used in data processing.

In the ophthalmic apparatus disclosed herein, the light source may be configured to sweep a wavelength of light in a wavelength range ranging from a first wavelength to a second wavelength. A waveform of the wavelength of the light from the light source may be a sine wave. The computer-readable instructions, when executed by the processor, further may cause the ophthalmic apparatus to: detect a time at which the period becomes a predetermined period in the period data; and determine a reference time based on the time at which the period becomes the predetermined period in the period data, the reference time being one reference time at which the period is at its maximum or its minimum in the period data or two reference times including a time at which the period is at its maximum and a time at which the period is at its minimum in the period data. The processing duration may be determined based on the determined reference time or the detected two reference times. According to this configuration, the light source of the wavelength sweeping type cyclically sweeps the wavelength of the light in the range from the first wavelength to the second wavelength, and the waveform of the light from the light source becomes a sine wave. Due to this, the period data of the sample clock signal generated from the light from the light source changes cyclically corresponding to the waveform of the sine wave. As such, by detecting the time at which the period becomes the predetermined period, the reference time at which the period is at its maximum or its minimum can be specified from the detected time. By determining the processing duration of the interference signal sampled based on the specified reference time, the interference signal sampled at the same timing each time the wavelength of the light undergoes one cycle of change can be used in data processing.

In the ophthalmic apparatus disclosed herein, the light source may be configured to sweep a wavelength of light in a wavelength range ranging from a first wavelength to a second wavelength. A waveform of the wavelength of the light from the light source may be a sawtooth wave. The computer-readable instructions, when executed by the processor, further may cause the ophthalmic apparatus to detect a reference time at which the period changes from a constant value in the period data. The processing duration may be determined based on the detected reference time. According to this configuration, the light source of the wavelength sweeping type cyclically sweeps the wavelength of the light in the wavelength range ranging from the first wavelength to the second wavelength, and the waveform of the light from the light source becomes a sawtooth wave. Due to this, the period data of the sample clock signal generated from the light from the light source is constant at respectively different values during increase and decrease of the wavelength of the light from the light source. As such, by setting the processing duration of the interference signal sampled with the time at which the period changes from a constant value in the period data as a reference, the interference signal sampled at the same timing each time the wavelength of the light undergoes one cycle of change can be used in data processing.

In the ophthalmic apparatus disclosed herein, the signal processor may be configured to sample the interference signal based on the determined processing duration. According to this configuration, the signal processor can sample the interference signal during the processing duration determined based on the period data. Due to this, the interference signal can be sampled at the same timing each time the wavelength of the light undergoes one cycle of change.

In the ophthalmic apparatus disclosed herein, the signal processor may be configured to sample the interference signal at least over the processing duration. The computer-readable instructions, when executed by the processor, further may cause the ophthalmic apparatus to extract the interference signal corresponding to the determined processing duration from the sampled interference signal. According to this configuration, the interference signal corresponding to the processing time determined based on the period data is extracted from the interference signal sampled by the signal processor. Due to this, the interference signal sampled at the same timing each time the wavelength of the light undergoes one cycle of change can be used in data processing.

EMBODIMENT

First Embodiment

An ophthalmic apparatus 1 of an embodiment will be described hereinbelow. As shown in FIG. 1, the ophthalmic apparatus 1 comprises a light source 12, a measurement unit 10 configured to examine a subject eye 100, and a K-clock generator 80. Light outputted from the light source 12 enters a beam splitter 18 and is split into light to be guided to the measurement unit 10 and light to be guided to the K-clock generator 80 in the beam splitter 18.

The measurement unit 10 comprises an interference optical system 14 configured to cause reference light to interfere with reflected light that is reflected from the subject eye 100, an observation optical system 50 configured to observe an anterior part of the subject eye 100, and an alignment optical system (not shown) configured to align the measurement unit 10 with respect to the subject eye 100 in a predetermined positional relationship. An alignment optical system that has been used in a well-known ophthalmic apparatus can be used as the aforementioned alignment optical system, and thus detailed explanation thereof is herein omitted.

The interference optical system 14 is constituted of a measurement optical system configured to irradiate an inside of the subject eye 100 with light from the light source 12 and guide reflected light therefrom, a reference optical system configured to irradiate a reference surface with light from the light source 12 and guide reflected light therefrom, and a light receiving element 26 configured to receive interference light in which the reflected light guided by the measurement optical system is combined with the reflected light guided by the reference optical system.

The light source 12 is a light source of a wavelength sweeping type, and is configured to change a wavelength of light outputted therefrom at a predetermined period. In this embodiment, the light source 12 outputs the light by changing the wavelength of the light such that a waveform of the wavelength of the light becomes a sine wave (see FIG. 6A). When the wavelength of the light outputted from the light source 12 changes, a reflection position of reflected light that interferes with the reference light among the light reflected from respective parts of the subject eye 100 in a depth direction changes in the depth direction of the subject eye 100 according to the wavelength of the outputted light. Due to this, by measuring the interference light while changing the wavelength of the outputted light, positions of the respective parts of the subject eye 100 (that is, crystalline lens 104 and retina 106) can be specified.

The measurement optical system is constituted of a beam splitter 24, a mirror 28, a 0-point (zero-point) adjustment mechanism 30, a mirror 34, a focal point adjustment mechanism 40, a Galvano scanner 46, and a hot mirror 48. Light outputted from the light source 12 is guided to the measurement unit 10 through the beam splitter 18. The light guided to the measurement unit 10 enters the subject eye 100 through the beam splitter 24, the mirror 28, the 0-point adjustment mechanism 30, the mirror 34, the focal point adjustment mechanism 40, the Galvano scanner 46, and the hot mirror 48. Reflected light from the subject eye 100 is guided to the light receiving element 26 through the hot mirror 48, the Galvano scanner 46, the focal point adjustment mechanism 40, the mirror 34, the 0-point adjustment mechanism 30, the mirror 28, and the beam splitter 24.

Figure 2:
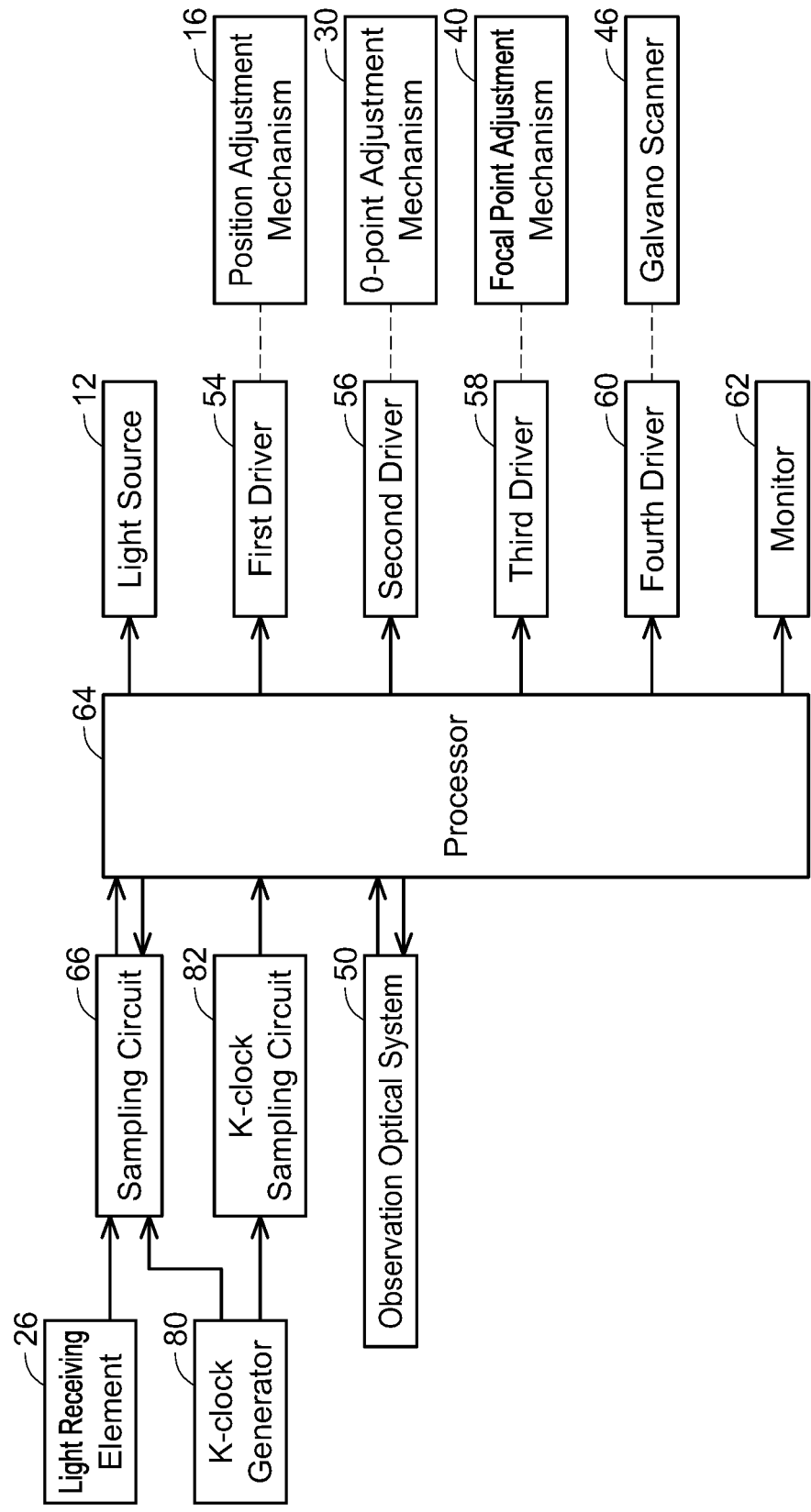
FIG. 2 is a block diagram of a control system of the ophthalmic apparatus according to the embodiment.
Figure 3:
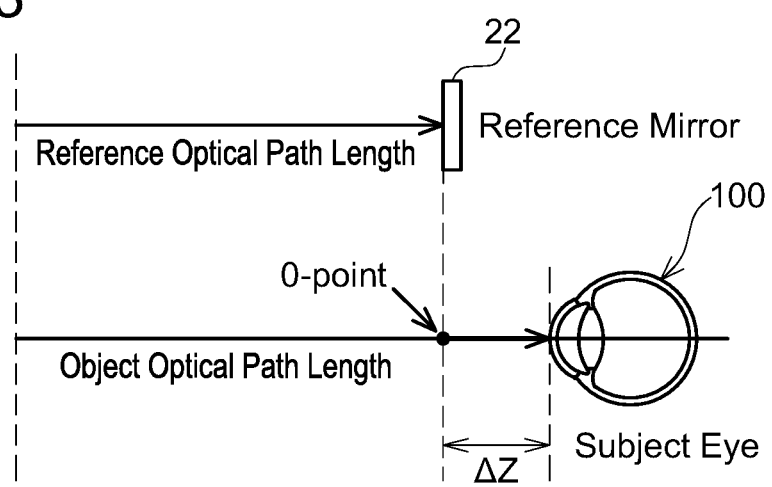
FIG. 3 is a diagram for explaining a function of a 0-point adjustment mechanism.

The 0-point adjustment mechanism 30 is provided with a corner cube 32, and a second driver 56 (shown in FIG. 2) configured to move the corner cube 32 back and forth with respect to the mirrors 28 and 34. When the second driver 56 moves the corner cube 32 in a direction of an arrow A in FIG. 1, an optical path length from the light source 12 to the subject eye 100 (that is, an object optical path length of the measurement optical system) changes. As shown in FIG. 3, when there is an optical path difference ΔZ between the object optical path length from the light source 12 to a detection surface (a corneal surface in FIG. 3) of the subject eye 100 (more specifically, from the light source 12 to the detection surface plus from the detection surface to the light receiving element 26) and the reference optical path length from the light source 12 to the reference mirror 22 (more specifically, from the light source 12 to the reference mirror 22 plus from the reference mirror 22 to the light receiving element 26), the larger the optical path difference ΔZ becomes, the lower an intensity of the interference light being a combination of the reference light and reflected light that is reflected from the detection surface becomes. Conversely, the smaller the optical path difference ΔZ becomes, the higher the intensity of the interference light becomes. Therefore, in the present embodiment, by changing the object optical path length with the 0-point adjustment mechanism 30, it is possible to change a position at which the reference optical path length and the object optical path length match (that is, the 0-point) from the surface of a cornea 102 to a surface of the retina 106.

The focal point adjustment mechanism 40 is provided with a convex lens 42 disposed on the light source 12 side, a convex lens 44 disposed on the subject eye 100 side, and a third driver 58 (shown in FIG. 2) that moves the convex lens 44 back and forth with respect to the convex lens 42 in an optical axis direction. The convex lens 42 and the convex lens 44 are disposed on the optical axis and change a position of a focal point of incident parallel light from the light source 12. Thus, when the third driver 58 drives the convex lens 44 in the direction of arrow B in FIG. 1, the position of the focal point of the light radiated to the subjected eye 100 changes in the depth direction of the subject eye 100, and the position of the focal point of the light radiated to the subject eye 100 is adjusted.

The Galvano scanner 46 includes a Galvano mirror 46a, and a fourth driver 60 (shown in FIG. 2) configured to tilt the Galvano mirror 46a. An irradiation position of the measurement light to the subject eye 100 is scanned by the fourth driver 60 tilting the Galvano mirror 46a.

The reference optical system is constituted of the beam splitter 24 and a reference mirror 22. A part of the light guided to the measurement unit 10 through the beam splitter 18 is reflected by the beam splitter 24, is directed to the reference mirror 22, and then is reflected by the reference mirror 22. The light reflected by the reference mirror 22 is guided to the light receiving element 26 through the beam splitter 24. The reference mirror 22, the beam splitter 24, and the light receiving element 26 are disposed in an interferometer 20, and their positions are fixed. Therefore, in the ophthalmic apparatus 1 of the present embodiment, a reference optical path length is constant and does not change.

The light receiving element 26 is configured to detect the interference light that is the combination of the light guided by the reference optical system and the light guided by the measurement optical system. The light receiving element 26 is configured to output interference signals according to the interference light when the light receiving element 26 receives the interference light. The interference signals are inputted to a processor 64 via a sampling circuit 66. A photodiode can be implemented for example as the light receiving element 26.

The observation optical system 50 irradiates the subject eye 100 with observation light through the hot mirror 48 and captures reflected light that is reflected from the subject eye 100 (that is, reflected light of the observation light). Here, the hot mirror 48 reflects the light from the light source 12 of the interference optical system 14 and transmits light from a light source of the observation optical system 50. As a result, in the ophthalmic apparatus 1 of the present embodiment, it is possible to perform the measurement by the interference optical system 14 and the observation of the anterior part of the eye by the observation optical system 50 at the same time. An observation optical system that has been used in a well-known ophthalmic apparatus can be used as the observation optical system 50. For this reason, detailed configuration thereof is not explained herein.

The K-clock generator 80 is configured to optically generate sample clock (K-clock) signals from the light split through the beam splitter 18 to sample the interference signals at a regular frequency interval (at interval regularly set relative to change in a frequency of light). Further, the generated K-clock signals are outputted toward the sampling circuit 66. The sampling circuit 66 samples the interference signals based on the K-clock signals, thus distortion in the interference signal can be suppressed, and deterioration in resolution can be prevented. Further, the K-clock generator 80 also outputs the generated K-clock signals to the processor 64 through a K-clock sampling circuit 82. The K-clock generator 80 is an example of a "sample clock signal generator".

The interference signals and the K-clock signals are inputted to the sampling circuit 66, and the interference signals are sampled at timings defined by the K-clock signals. A well-known data aquisition apparatus (so-called DAQ) may be used as the sampling circuit 66. The sampling circuit 66 is configured to sample the interference signals to acquire A-scan information regarding the inside of the subject eye 100 (which is information indicating a relationship between a depthwise position of an internal structure of the subject eye 100 along a measurement optical axis and a signal intensity).

Further, the ophthalmic apparatus 1 of the embodiment is provided with a position adjustment mechanism 16 (shown in FIG. 2) configured to adjust a position of the measurement unit 10 (more specifically, an optical system being a portion of the measurement unit 10 excluding the interferometer 20) with respect to the subject eye 100, and a first driver 54 (shown in FIG. 2) configured to drive the position adjustment mechanism 16. The position adjustment mechanism 16 is driven by the first driver 54 in accordance with an operation by an examiner on an operation member, by which the positions of the measurement unit 10 in xy directions (vertical and lateral directions) and in a z direction (a direction of moving back and forth) with respect to the subject eye 100 are adjusted.

Next, a configuration of a control system of the ophthalmic apparatus 1 according to the present embodiment will be described. As shown in FIG. 2, the ophthalmic apparatus 1 is controlled by the processor 64. The processor 64 includes a microcomputer (microprocessor) configured of CPU, ROM, RAM, and the like. The processor 64 is connected to the light source 12, the first to forth drivers 54 to 60, a monitor 62, and the observation optical system 50. The processor 64 is configured to control on/off of the light source 12, and drive the position adjuster 16, the 0-point adjustment mechanism 30, the focal point adjustment mechanism 40, and the Galvano scanner 46 by controlling the first to forth drivers 54 to 60. Further, the processor 64 is configured to control the observation optical system 50 to display an image of the anterior eye part captured by the observation optical system 50 on the monitor 62.

Figure 4:
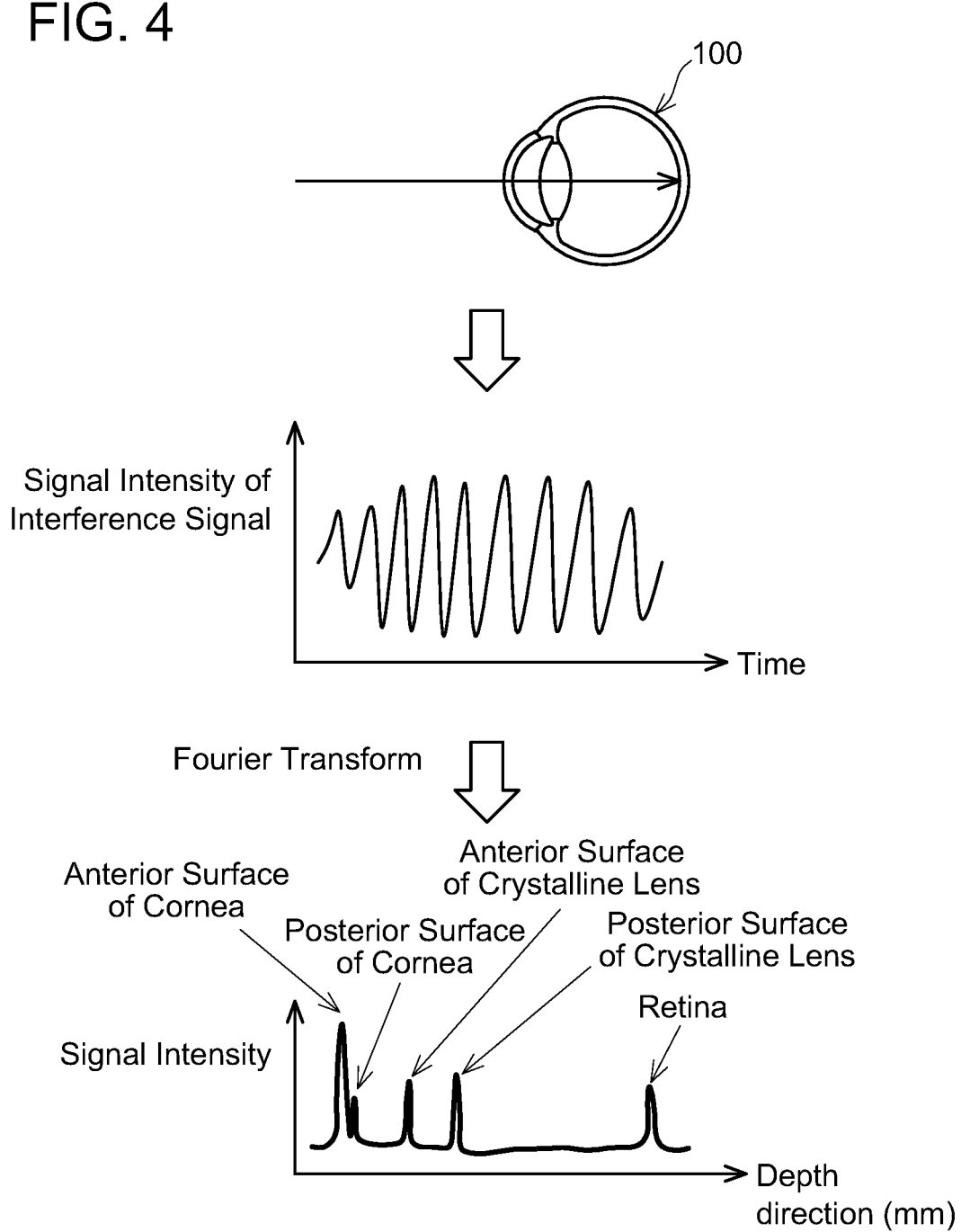
FIG. 4 shows diagrams for explaining a procedure to process an interference signal waveform.

Further, the processor 64 has the sampling circuit 66 and the K-clock sampling circuit 82 connected thereto. The K-clock signal generated in the K-clock generator 80 is inputted to the processor 64 through the K-clock sampling circuit 82, and the processor 64 is configured to generate a trigger signal that defines start of sampling based on the K-clock signal. Generation of the trigger signal in the processor 64 will be described later. The processor 64 is configured to output the generated trigger signal to the sampling circuit 66. When the trigger signal is inputted, the sampling circuit 66 acquires the interference signal at timings defined by the K-clock signal during a preset time. The interference signal sampled in the sampling circuit 66 is inputted to the processor 64. As aforementioned, the interference signal outputted from the light receiving element 26 becomes a signal of which signal intensity changes over time as shown in FIG. 4, and this signal includes a signal of an interference wave which is a combination of the reference light and each of the reflected light reflected from the respective parts of the subject eye 100 (anterior and posterior surfaces of the cornea 102, anterior and posterior surfaces of the crystalline lens 104, and the surface of the retina 106). The processor 64 is configured to Fourier-transform the sampled interference signal, and separate interference signal components of the respective parts of the subject eye 100 (the anterior and posterior surfaces of the cornea 102, the anterior and posterior surfaces of the crystalline lens 104, and the surface of the retina 106) from within the interference signal (see a graph on a lower side in FIG. 4). By doing so, the processor 64 can specify positions of the respective parts of the subject eye 100.

Next, a process of generating the trigger signal in the ophthalmic apparatus 1 of the present embodiment will be described. In the ophthalmic apparatus 1 of the present embodiment, the wavelength sweeping type light source 12 is used, so the wavelength of the light outputted from the light source 12 cyclically changes. In a case of using such a light source 12, distortion in the interference signal can be suppressed by performing the sampling in a same wavelength range each time the wavelength of the light outputted from the light source 12 undergoes one cycle of change. Further, as aforementioned, in sampling the interference signal in the sampling circuit 66, the trigger signal is inputted from the processor 64 to start the sampling at the timing defined by the trigger signal. As such, the processor 64 generates the trigger signal to define the timings at which the wavelength of the light outputted form the light source 12 would have a same wavelength each time the wavelength of the light undergoes one cycle of change. Generally, upon generating the trigger signal, light of a particular wavelength is detected, and the trigger signal is generated from the light of the detected wavelength. Fiber Bragg grating (FBG) or etalon is used for detection of the particular wavelength. The ophthalmic apparatus 1 of the present embodiment uses the K-clock signal for sampling the interference signal to generate the trigger signal without using costly members such as the FBG and the etalon. Hereinbelow, the process of generating the trigger signal will be described with reference to FIGS. 5 and 6.

Figure 5:
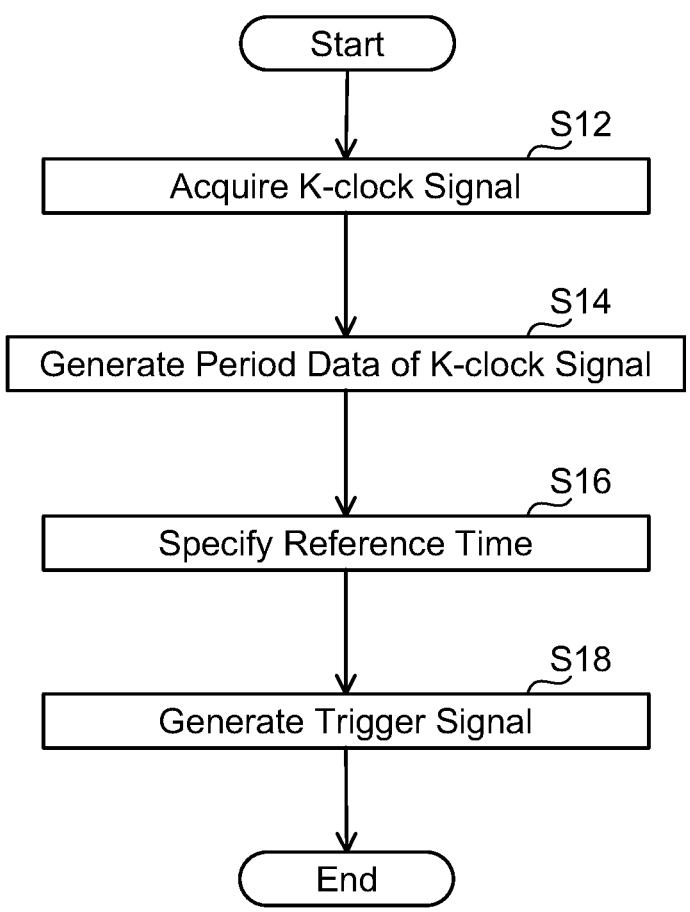
FIG. 5 is a flowchart showing an example of a process of generating a trigger signal.

As shown in FIG. 5, firstly, the processor 64 acquires the K-clock signal generated in the K-clock generator 80 and sampled by the K-clock sampling circuit 82 (S12). As aforementioned, the K-clock generator 80 generates the K-clock signal which cyclically changes at equal frequency intervals from the light outputted from the light source 12. The K-clock generator 80 outputs the generated K-clock signal to the K-clock sampling circuit 82, and the K-clock sampling circuit 82 samples the K-clock signal. The sampled K-clock signal is inputted to the processor 64.

Figure 6A:
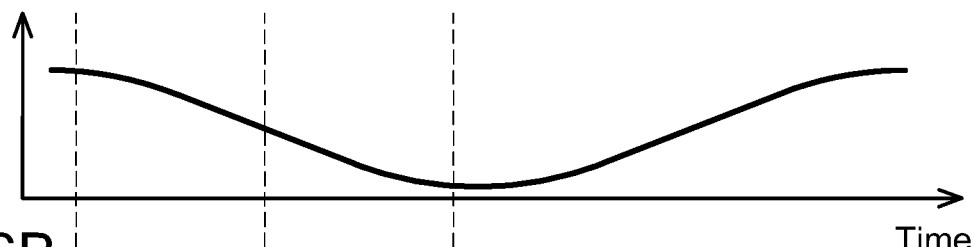
FIGS. 6A to 6D are diagrams showing a relationship between a K-clock signal and light outputted from a light source when a waveform of a wavelength of the light outputted from the light source is a sine wave, where
Figure 6B:
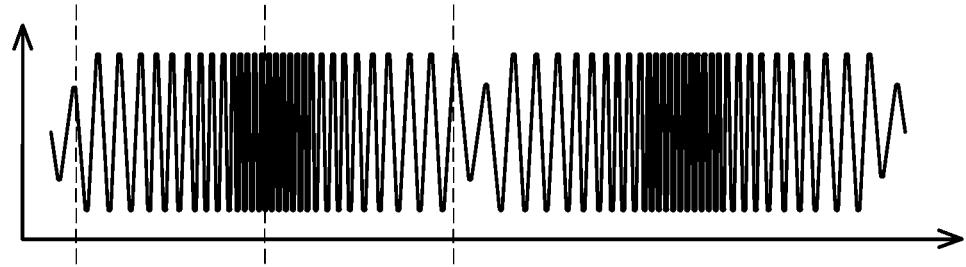
Figure 6C:
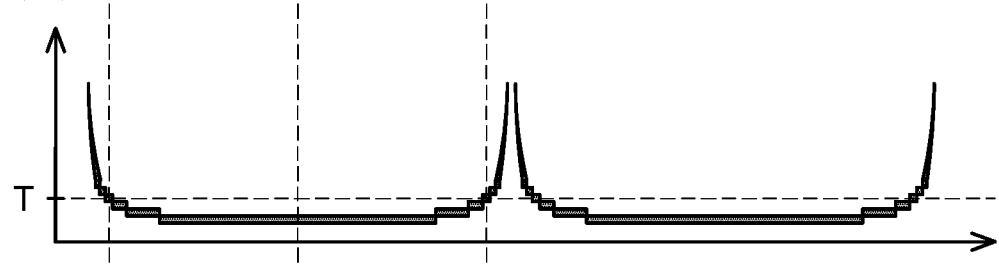
Figure 6D:
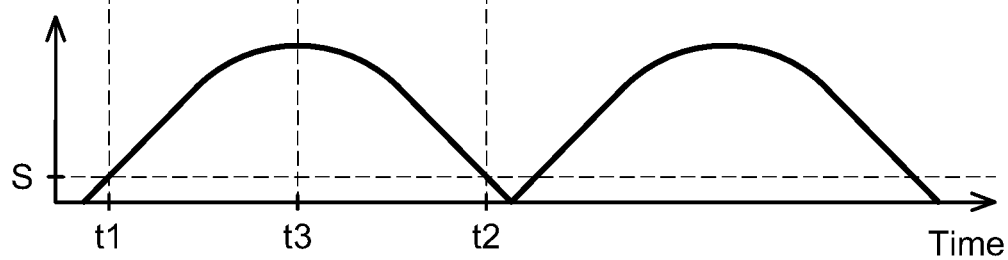

Here, a relationship between the light outputted from the light source 12 and the K-clock signal will be described with reference to FIGS. 6A to 6D. FIG. 6A shows a relationship between the wavelength of the light outputted from the light source 12 and time, FIG. 6B shows a relationship between a signal intensity of the K-clock signal and the time, FIG. 6C shows period data of the K-clock signal, and FIG. 6D shows a relationship between a frequency of the K-clock signal and the time.

The light source 12 outputs the light of which wavelength is changed at a predetermined period. In this embodiment, as shown in FIG. 6A, the waveform of the wavelength of the light outputted from the light source 12 is a sine wave, so the K-clock signal changes cyclically at equal frequency intervals. As shown in FIGS. 6B and 6D, the waveform of the signal intensity of the K-clock signal has wide peak intervals when the frequency of the K-clock signal is small, and has narrow peak intervals when the frequency of the K-clock signal is large. Further, in terms of the relationship between the signal intensity of the K-clock signal and the wavelength of the light outputted from the light source 12, the waveform of the signal intensity of the K-clock signal has wide peak intervals when the change in the wavelength of the light outputted from the light source 12 (an inclination of the waveform) is small, and has narrow peak intervals when the change in the wavelength of the light outputted from the light source 12 (the inclination of the waveform) is large, as shown in FIGS. 6A and 6B.

Next, the processor 64 generates the period data indicating the relationship between the period of the K-clock signal and the time from the K-clock signal acquired in step S12 (S14). The processor 64 calculates the period of the K-clock signal from the relationship of the signal intensity of the K-clock signal and the time (see FIG. 6B), and generates data indicating a relationship between the period of the K-clock signal and a period data number. In this data, the period data number and the time correspond to each other. Due to this, hereinbelow, the data indicating the relationship between the period of the K-clock signal and the time will be termed "K-clock signal period data". FIG. 6C shows the K-clock signal period data. As shown in FIGS. 6B and 6C, the period of the K-clock signal becomes large when the waveform of the signal intensity of the K-clock signal has wide peak intervals, and becomes small when the waveform of the signal intensity of the K-clock signal has narrow peak intervals. Further, in terms of the relationship between the period of the K-clock signal and the wavelength of the light outputted from the light source 12, the period of the K-clock signal becomes large when the change in the wavelength of the light outputted from the light source 12 (the inclination of the waveform) is small, and becomes small when the change in the wavelength of the light outputted from the light source 12 (the inclination of the waveform) is large, as shown in FIGS. 6A and 6C. Further, at timings when the change in the wavelength of the light (the inclination of the waveform) switches from increasing trend to decreasing trend or from the decreasing trend to the increasing trend, the period of the K-clock signal becomes infinite due to the inclination of the waveform becoming 0.

Next, the processor 64 specifies a reference time from the period data generated in step S14 (S16). The reference time is a time that is set as a reference upon generating the trigger signal, and in this embodiment, the time at which the period of the K-clock signal becomes minimum is set as the reference time.

The reference time is specified by the following procedure. As shown in FIG. 6C, the processor 64 detects a time t1 and a time t2 constituting a predetermined period T in the K-clock signal period data. Then, the processor 64 calculates a time t3, which is a midpoint between the detected time t1 and time t2 (that is, (t1+t2)/2). As shown in FIGS. 6C and 6D, the time t1 and the time t2 constituting the predetermined period T correspond to a time at which a predetermined frequency S is achieved, and the time t3 being the midpoint between the time t1 and time t2 corresponds to a time when the frequency becomes maximum. As such, the period of the K-clock signal becomes minimum at the time when the frequency of the light outputted from the light source 12 becomes maximum (time t3). The reference time at which the period of the K-clock signal becomes minimum is detected as above. By specifying the reference time by the above procedure, the reference time can be specified even in a case where the time at which the period of the K-clock signal becomes minimum cannot be detected accurately. In this embodiment, the reference time is detected from the time t1 and t2 constituting the predetermined period T, however, no limitation is made to this configuration. For example, in a case where a time at which the period of the K-clock signal becomes minimum can be detected accurately, the time at which the period of the K-clock signal becomes minimum may be directly detected. That is, in a case where measurement accuracy of the signal intensity of the K-clock signal is sufficiently high, an inflection point at which the period data changes from the decreasing trend to the increasing trend can be specified accurately, so the time at which the period of the K-clock signal becomes minimum may be directly specified.

Next, the processor 64 generates the trigger signal based on the reference time detected in step S16 (S18). In this embodiment, the reference time is the time t3 at which the period of the K-clock signal becomes minimum, and is a time at which the change in the wavelength of the light outputted from the light source 12 (the inclination of the waveform) becomes maximum (see FIGS. 6A and 6C). When the waveform of the wavelength of the light outputted from the light source 12 is a sine wave, the sampling of the interference signal is preferably performed in a wavelength range where the change in the wavelength of the light outputted from the light source 12 is large. That is, it is preferable to sample the interference signal before and after the time at which the period of the K-clock signal becomes minimum. The processor 64 generates the trigger signal that defines a time at which a predetermined time has elapsed from the reference time t3 such that the interference signal is sampled before and after the time at which the period of the K-clock signal becomes minimum in a period that follows the period in which the reference time t3 was detected. By performing the sampling based on the trigger signal generated as above, the interference signal can be sampled in the same wavelength range each time the wavelength of the light outputted from the light source 12 undergoes one cycle of change without detecting the particular wavelength using the costly members such as the FGB and the etalon.

In the present embodiment, the time at which the period of the K-clock signal becomes minimum is set as the reference time, however, no limitation is made to this configuration. The reference time may simply need to correspond to a time at which the wavelength of the light outputted from the light source 12 becomes a particular wavelength, and for example, a time at which the period of the K-clock signal becomes maximum may be set as the reference time. With such a reference time, the wavelength of the light outputted from the light source 12 becomes maximum or minimum (see FIGS. 6A and 6C). In this case as well, the reference time may be specified based on a time pair constituting a predetermined period, or the time at which the period of the K-clock signal becomes maximum (the reference time) may be directly detected. Further, in a case of setting the reference time as above, the processor 64 may generate the trigger signal that defines a time at which a predetermined time has elapsed from the reference time in the period in which the reference time was detected. Even by generating the trigger signal as above, the interference signal can be sampled in the same wavelength range each time the wavelength of the light outputted from the light source 12 undergoes one cycle of change.

Second Embodiment

Figure 7A:
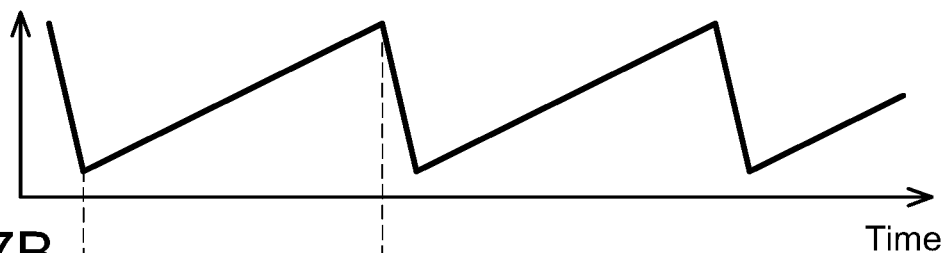
FIGS. 7A to 7C are diagrams showing a relationship between the K-clock signal and the light outputted from the light source when the waveform of the wavelength of the light outputted from the light source is a sawtooth wave, where
Figure 7B:
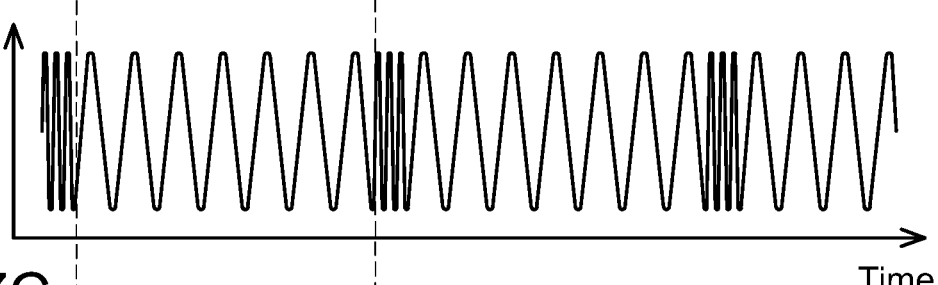
Figure 7C:
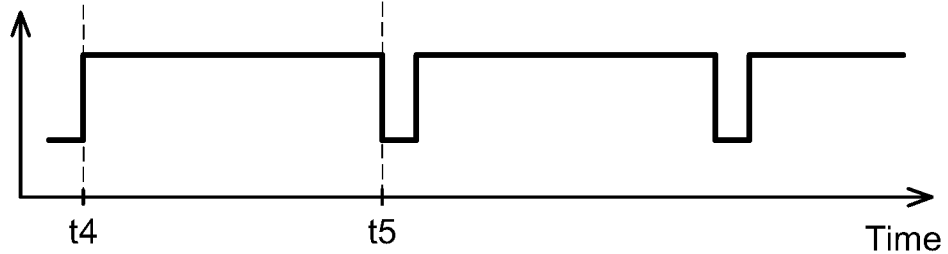

The first embodiment as above used the waveform of the wavelength of the light outputted from the light source 12 being a sine wave, however, no limitation is made to this configuration. The wavelength of the light outputted from the light source may simply need to change at a predetermined period, and for example, the waveform of the wavelength of the light outputted from the light source may be a sawtooth wave. Hereinbelow, a process in which the processor 64 generates the trigger signal in a case where the waveform of the wavelength of the light outputted from the light source is a sawtooth wave will be described with reference to FIGS. 7A to 7C. FIG. 7A shows a relationship between the wavelength of the light outputted from the light source and the time, FIG. 7B shows a relationship between the signal intensity of the K-clock signal and the time, and FIG. 7C shows the K-clock signal period data.

Firstly, the processor 64 performs the process of step S12 of FIG. 5. That is, the processor 64 acquires the K-clock signal from the K-clock generator 80. As shown in FIG. 7A, in the case where the waveform of the wavelength of the light outputted from the light source is a sawtooth wave, the wavelength of the light increases relatively moderately at a certain rate, and once the wavelength reaches its maximum, it decreases relatively drastically at a certain rate until the wavelength reaches its minimum. As aforementioned, the waveform of the signal intensity of the K-clock signal has wide peak intervals when the change in the wavelength of the light outputted from the light source 12 (the inclination of the waveform) is small, and has narrow peak intervals when the change in the wavelength of the light outputted from the light source 12 (the inclination of the waveform) is large. Due to this, as shown in FIG. 7B, while the wavelength of the light outputted from the light source decreases drastically, the waveform of the signal intensity of the K-clock signal has narrow peak intervals, and since the wavelength of the light outputted from the light source decreases at a certain rate, peak intervals of the waveform of the signal intensity become substantially constant. Further, while the wavelength of the light outputted from the light source increases moderately, the waveform of the signal intensity of the K-clock signal has wide peak intervals, and since the wavelength of the light outputted from the light source increases at a certain rate, peak intervals of the waveform of the signal intensity become substantially constant.

Next, the processor 64 performs the process of step S14 of FIG. 5. That is, the processor 64 generates the period data indicating the relationship between the period of the K-clock signal and the time from the K-clock signal acquired in step S12. The processor 64 calculates the period of the K-clock signal from the relationship between the signal intensity of the K-clock signal and the time (see FIG. 7B) and generates the K-clock signal period data. As aforementioned, the period of the K-clock signal is large when the waveform of the signal intensity of the K-clock signal has wide peak intervals, and is small when the waveform of the signal intensity of the K-clock signal has narrow peak intervals. Due to this, as shown in FIGS. 7A to 7C, the period of the K-clock signal becomes constant at a small value while the wavelength of the light outputted from the light source decreases drastically. Further, the period of the K-clock signal becomes constant at a large value while the wavelength of the light outputted from the light source increases moderately.

Next, the processor 64 performs the process of step S16 of FIG. 5. That is, the processor 64 detects the reference time from the period data generated in step S14. In this embodiment, the reference time is a time when a value of the period of the K-clock signal changes. Due to this, a start time of a duration in which the wavelength of the light outputted from the light source increases (for example, a time t4 of FIG. 7C) and an end time thereof (for example, a time t5 of FIG. 7C) can be detected.

Next, the processor 64 performs the process of step S18 of FIG. 5. That is, the processor 64 generates the trigger signal based on the reference time detected in step S16. As shown in FIG. 7A, in this embodiment, since the wavelength of the light outputted from the light source increases moderately from its minimum value to maximum value, a time required for the increase of the wavelength of the light outputted from the light source is extended. Due to this, the processor 64 generates the trigger signal such that the interference signal is sampled while the wavelength of the light outputted from the light source increases. Specifically, the processor 64 generates the trigger signal that defines a time at which a predetermined time has elapsed from the start time t4 of the duration in which the wavelength of the light outputted from the light source increases. Due to this, the processor 64 can generate the trigger signal that defines the time at which the same wavelength is achieved each time the wavelength of the light outputted from the light source undergoes one cycle of change even in a case where the waveform of the wavelength of the light outputted from the light source is a sawtooth wave.

In the present embodiment, the waveform of the wavelength of the light outputted from the light source increases moderately at the certain rate until the wavelength reaches its maximum and decreases relatively drastically at the certain rate until the wavelength reaches its minimum, however, no limitation is made to this configuration. For example, the waveform of the wavelength of the light may decrease relatively moderately at a certain rate until the wavelength reaches its minimum, and increase relatively drastically at a certain rate until the wavelength reaches its maximum.

Third Embodiment

Figure 8A:
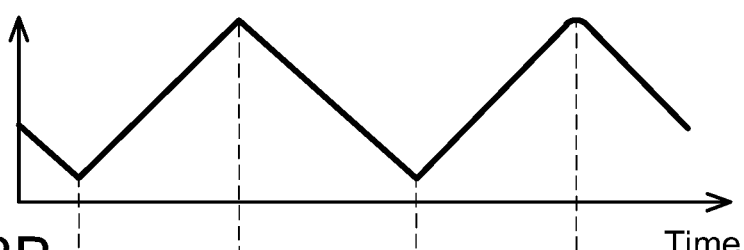
FIGS. 8A to 8C are diagrams showing a relationship between the K-clock signal and the light outputted from the light source when the waveform of the wavelength of the light outputted from the light source is a triangular wave, where
Figure 8B:
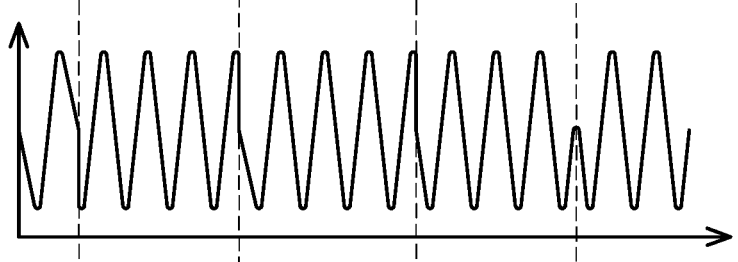
Figure 8C:
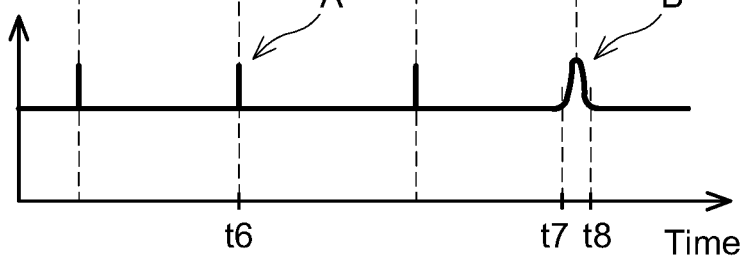

In the aforementioned second embodiment, the waveform of the wavelength of the light outputted from the light source is a sawtooth wave, however, the waveform of the wavelength of the light outputted from the light source may be a triangular wave. Hereinbelow, a process by which the processor 64 generates the trigger signal in a case where the waveform of the wavelength of the light outputted from the light source is a triangular wave will be described with reference to FIGS. 8A to 8C. FIG. 8A shows a relationship between the wavelength of the light outputted from the light source and the time, FIG. 8B shows a relationship between the signal intensity of the K-clock signal and the time, and FIG. 8C shows K-clock signal period data.

Firstly, the processor 64 acquires the K-clock signal from the K-clock generator 80 (step S12 of FIG. 5). As shown in FIG. 8A, in the case where the waveform of the wavelength of the light outputted from the light source is the triangular wave, the wavelength of the light increases at a certain rate and decreases at a certain rate between a maximum value and a minimum value of the wavelength. Due to this, the waveform of the signal intensity of the K-clock signal has substantially equal peak intervals while the wavelength of the light outputted from the light source increases, and the peak intervals also become substantially constant while the wavelength of the light outputted from the light source decreases. Further, the wavelength of the light outputted from the light source changes at the same rate when it increases and decreases. Due to this, as shown in FIG. 8B, the waveform of the signal intensity of the K-clock signal has substantially constant peak intervals over the entire time. However, when the wavelength of the light outputted from the light source changes between the increasing and decreasing trends, that is, when the wavelength of the light switches from the increasing trend to the decreasing trend and when it switches from the decreasing trend to the increasing trend, the change in the wavelength of the light outputted from the light source becomes discontinuous, and noise is generated in the waveform of the signal intensity of the K-clock signal.

Next, the processor 64 generates the period data indicating the relationship between the period of the K-clock signal and the time from the K-clock signal acquired in step S12 (step S14 of FIG. 5). The processor 64 calculates the period of the K-clock signal from the relationship between the signal intensity of the K-clock signal and the time (see FIG. 8B) and generates the K-clock signal period data. As aforementioned, since the waveform of the signal intensity of the K-clock signal shown in FIG. 8B has the substantially constant peak intervals over the entire time, the period of the K-clock signal becomes substantially constant. However, since noise is generated in the waveform of the signal intensity of the K-clock signal when the wavelength of the light outputted from the light source changes between the increasing and decreasing trends, the period of the K-clock signal is detected at a different value during such a time.

Next, the processor 64 detects the reference time from the period data generated in step S14 (step S16 of FIG. 5). In this embodiment, a time at which the period of the K-clock signal changes is set as the reference time. Due to this, the time at which the wavelength of the light outputted from the light source shifts between a duration in which it increases and a duration in which it decreases can be detected. For example, when the shift in the wavelength of the light outputted from the light source between the increasing and decreasing trends is performed within a short time (being in a state shown by A in FIG. 8C), a time during which the period of the K-clock signal is detected as a different value also becomes short. In such a case, a time at which the value of the period of the K-clock signal changes (such as a time t6 of FIG. 8C) is detected as the reference time. Further, when the shift in the wavelength of the light outputted from the light source between the increasing and decreasing trends is not performed within a short time (being in a state shown by B in FIG. 8C), the time during which the period of the K-clock signal is detected as a different value becomes relatively long. In such a case, the duration time in which the value of the period of the K-clock signal changes (such as the time t7 to the time t8 of FIG. 8C) may be detected by differentiating the K-clock signal period data, and then an intermediate time therebetween may be set as the reference time.

Next, the processor 64 generates the trigger signal based on the reference time detected in step S16 (step S18 of FIG. 5). As shown in FIG. 8A, in this embodiment, the wavelength of the light outputted from the light source increases at a certain rate and decreases at a certain rate between the maximum value and the minimum value of the wavelength.

Due to this, the processor 64 generates the trigger signal such that the interference signal is sampled in both when the wavelength of the light outputted from the light source is increasing and when it is decreasing. Specifically, the processor 64 generates the trigger signal that defines a time at which a predetermined time has elapsed from the reference time detected in step S16. By doing so, the processor 64 can generate the trigger signal that defines the time at which the same wavelength is achieved each time the wavelength of the light outputted from the light source undergoes one cycle of change even in the case where the waveform of the wavelength of the light outputted from the light source is a triangular wave.

In the first to third embodiments as above, the trigger signal is generated based on the K-clock signal period data and the interference signal is sampled in the sampling circuit 66 based on the generated trigger signal, however, no limitation is made to this configuration. The interference signal sampled in the predetermined wavelength range simply needs to be acquired based on the K-clock signal period data, thus for example, the processor 64 may acquire the interference signal first, and may extract the interference signal corresponding to a duration determined based on the K-clock signal period data. Specifically, the processor 64 acquires the interference signal sampled at equal frequency intervals defined by the K-clock signal from the sampling circuit 66. In doing so, the sampling circuit 66 samples the interference signal so as to include the predetermined wavelength range required for data processing (hereinbelow termed a processing duration), in a duration that is longer than the processing duration. Then, the processor 64 specifies reference time by one of the processes of the first to third embodiments (specifically, the processes of steps S12 to S16 of FIG. 5). Then, the processor 64 determines the processing duration based on the specified reference time, and extracts the interference signal corresponding to the determined processing duration from the acquired interference signal. In this case as well, the interference signal sampled in the same wavelength range can be acquired each time the wavelength of the light outputted from the light source 12 undergoes one cycle of change.

While specific examples of the present disclosure have been described above in detail, these examples are merely illustrative and place no limitation on the scope of the patent claims. The technology described in the patent claims also encompasses various changes and modifications to the specific examples described above. The technical elements explained in the present description or drawings provide technical utility either independently or through various combinations. The present disclosure is not limited to the combinations described at the time the claims are filed.

What is claimed is:

1. An ophthalmic apparatus comprising:
a light source of wavelength sweeping type;
a measurement optical system configured to irradiate a subject eye with light from the light source and to guide reflected light from the subject eye;
a reference optical system configured to guide the light from the light source so as to use the light from the light source as reference light;
a light receiving element configured to receive interference light, the interference light being a combination of the reflected light from the subject eye and the reference light;
a sample clock signal generator configured to generate a sample clock signal from the light from the light source, the sample clock signal cyclically changing at equal frequency intervals;
a signal processor configured to sample an interference signal based on the sample clock signal outputted from the sample clock signal generator, the interference signal being outputted from the light receiving element when the light receiving element receives the interference light;
a processor; and
a memory storing computer-readable instructions therein, wherein
the computer-readable instructions, when executed by the processor, cause the ophthalmic apparatus to:
generate period data based on the sample clock signal, the period data indicating a relationship between a period of the sample clock signal and time; and
determine a processing duration of the interference signal sampled at the signal processor based on the period data.

2. The ophthalmic apparatus according to claim 1, wherein
the light source is configured to sweep a wavelength of light in a wavelength range ranging from a first wavelength to a second wavelength,
the computer-readable instructions, when executed by the processor, further cause the ophthalmic apparatus to detect one reference time at which the period is at its maximum or its minimum in the period data or two reference times including a time at which the period is at its maximum and a time at which the period is at its minimum in the period data, and
the processing duration is determined based on the detected reference time or the detected two reference times.

3. The ophthalmic apparatus according to claim 1, wherein
the light source is configured to sweep a wavelength of light in a wavelength range ranging from a first wavelength to a second wavelength,
a waveform of the wavelength of the light from the light source is a sine wave,
the computer-readable instructions, when executed by the processor, further cause the ophthalmic apparatus to:
detect a time at which the period becomes a predetermined period in the period data; and
determine a reference time based on the time at which the period becomes the predetermined period in the period data, the reference time being one reference time at which the period is at its maximum or its minimum in the period data or two reference times including a time at which the period is at its maximum and a time at which the period is at its minimum in the period data, and
the processing duration is determined based on the determined reference time or the determined two reference times.

4. The ophthalmic apparatus according to claim 1, wherein
the light source is configured to sweep a wavelength of light in a wavelength range ranging from a first wavelength to a second wavelength,
a waveform of the wavelength of the light from the light source is a sawtooth wave,
the computer-readable instructions, when executed by the processor, further cause the ophthalmic apparatus to detect a reference time at which the period changes from a constant value in the period data, and the processing duration is determined based on the detected reference time.

5. The ophthalmic apparatus according to claim 1, wherein the signal processor is configured to sample the interference signal based on the determined processing duration.

6. The ophthalmic apparatus according to claim 1, wherein the signal processor is configured to sample the interference signal at least over the processing duration, and the computer-readable instructions, when executed by the processor, further cause the ophthalmic apparatus to extract the interference signal corresponding to the determined processing duration from the sampled interference signal.

* * * * *